(12) United States Patent
Webster et al.

(10) Patent No.: US 7,943,163 B2
(45) Date of Patent: May 17, 2011

(54) MEDICAL FOOD OR NUTRITIONAL SUPPLEMENT, METHOD OF MANUFACTURING SAME, AND METHOD OF MANAGING DIABETES

(75) Inventors: Gregory D. Webster, Orlando, FL (US); Emmanuel C. Opara, Durham, NC (US)

(73) Assignee: Response Scientific, Inc., Princeton, NJ (US)

( * ) Notice: Subject to any disclaimer, the term of this patent is extended or adjusted under 35 U.S.C. 154(b) by 103 days.

(21) Appl. No.: 11/843,525

(22) Filed: Aug. 22, 2007

(65) Prior Publication Data

US 2009/0053303 A1  Feb. 26, 2009

(51) Int. Cl.
*A61K 47/00* (2006.01)

(52) U.S. Cl. ........................................ 424/439
(58) Field of Classification Search .................. None
See application file for complete search history.

(56) References Cited

U.S. PATENT DOCUMENTS

| | | | |
|---|---|---|---|
| 5,118,505 A | 6/1992 | Költringer | |
| 5,532,269 A | 7/1996 | Költringer | |
| 5,569,670 A | 10/1996 | Weischer et al. | |
| 5,650,429 A | 7/1997 | Conrad et al. | |
| 5,693,664 A | 12/1997 | Wessel et al. | |
| 5,886,037 A * | 3/1999 | Klor et al. ..................... | 514/546 |
| 5,948,810 A | 9/1999 | Wessel et al. | |
| 5,962,030 A | 10/1999 | Fine | |
| 5,977,162 A | 11/1999 | Seidman | |
| 5,990,153 A | 11/1999 | Wood et al. | |
| 6,117,899 A | 9/2000 | Wessel et al. | |
| 6,203,819 B1 | 3/2001 | Fine | |
| 6,251,935 B1 | 6/2001 | Schoenen et al. | |
| 6,284,787 B1 | 9/2001 | Wessel et al. | |
| 6,288,106 B1 | 9/2001 | Pearson et al. | |
| 6,339,102 B1 | 1/2002 | Meyerhoff et al. | |
| 6,365,622 B1 | 4/2002 | Cavazza | |
| 6,376,549 B1 | 4/2002 | Fine et al. | |
| 6,413,946 B1 | 7/2002 | Niizato et al. | |
| 6,440,951 B1 | 8/2002 | Niizato et al. | |
| 6,469,049 B1 | 10/2002 | Meyerhoff et al. | |
| 6,545,039 B1 | 4/2003 | Auge et al. | |
| 6,579,544 B1 | 6/2003 | Rosenberg et al. | |
| 6,579,866 B2 * | 6/2003 | McCleary ..................... | 514/188 |
| 6,585,998 B2 | 7/2003 | Cartwright et al. | |
| 6,733,793 B2 | 5/2004 | Pacioretty et al. | |
| 6,852,760 B1 | 2/2005 | Fine et al. | |
| 6,887,894 B2 | 5/2005 | Krämer et al. | |
| 6,964,969 B2 * | 11/2005 | McCleary ..................... | 514/283 |
| 2007/0009608 A1 | 1/2007 | Berge et al. | |
| 2007/0037826 A1 | 2/2007 | Evenou et al. | |
| 2007/0155735 A1 | 7/2007 | Lesuisse et al. | |
| 2007/0203134 A1 | 8/2007 | Schwarz et al. | |

OTHER PUBLICATIONS

Fernandez-Mejia, Pharmacological Effects of Biotin, J of Nutritional Biochemistry 16, 2005, 424-427.*
Hidgson et al, CoEnzyme Q-10 Improves Blood Pressure and Glycaemic Control, European J of Clinical Nutrition (2002) 56, 1137-1142.*
Ruhe et al, Use of Antioxidant Nutrients in the PRevention and Treatment of Type 2 Diabetes.*
Higdon (Linus Pauling Institute, Essential Omega Fatty Acids, http://web.archive.org/web/20060408222428/http://lpi.oregonstate.edu/infocenter/.. (Apr. 8, 2006). p. 1-18.*
Ruhe et al, Use of Antioxidant Nutrients in the Prevention and Treatment of Type 2 Diabetes, 2001.*
USPTO Office Action for U.S. Appl. No. 11/855,808, May 15, 2009, pp. 1-16.
Amendment and Response to Office Action for U.S. Appl. No. 11/855,808, filed Nov. 9, 2009, pp. 1-16.
Meletis, C. et al. "Natural Approaches for Treating Polycystic Ovary Syndrome"; Alternative & Complimentary Therapies; Aug. 2006; vol. 12, No. 4; pp. 157-164.

* cited by examiner

*Primary Examiner* — Tracy Vivlemore
*Assistant Examiner* — Jennifer A Berríos
(74) *Attorney, Agent, or Firm* — Hogan Lovells US LLP

(57) ABSTRACT

A medical food and/or nutritional supplement for oral administration by mammals includes α-lipoic acid, linolenic acid complex, biotin, and coenzyme Q-10. A preferred method of manufacturing the medical food or nutritional supplement is by separate microencapsulation of one or more of the components followed by encapsulation of the individual components, for oral administration. Other methods of delivery include packaging in impermeable, disposable packets and mixing the formulations with food or a cold liquid.

8 Claims, No Drawings

MEDICAL FOOD OR NUTRITIONAL SUPPLEMENT, METHOD OF MANUFACTURING SAME, AND METHOD OF MANAGING DIABETES

FIELD OF THE INVENTION

The present invention relates to medical foods and nutritional supplements and methods of using and manufacturing same. More particularly, the present invention relates to the medical foods and nutritional supplements which may be used to manage blood glucose levels, prevent the onset of type 2 diabetes, or manage diabetes mellitus.

BACKGROUND OF THE INVENTION

Diabetes mellitus includes diabetes mellitus types 1 and 2. Diabetes mellitus type 2 (sometimes referred to as diabetes mellitus type II and adult-onset diabetes) is a metabolic disorder typically involving insulin resistance, in which the cells of the body of an individual do not respond appropriately when insulin is present. If unnoticed or left untreated, severe complications can result, including renal failure, blindness and wounds that fail to heal. While there is an inheritable genetic connection, more than 80% of the individuals with diabetes type 2 are overweight or obese. Diabetes mellitus type 1 usually results from an autoimmune disorder that destroys pancreatic beta cells which produce insulin.

Metformin (1-(diaminomethylidene)-3,3-dimethyl-guanidine) is an anti-diabetic drug having the formula $C_4H_{11}N_5$. available by prescription under the trade names Glucophage™, Diabex™, Diaformin™ and others, with generic forms available. Metformin appears to reduce hepatic gluconeogenesis, decrease absorption of glucose from the gastrointestinal tract and increase insulin sensitivity. Adverse effects include impaired liver or kidney function, diarrhea, cramps, nausea, vomiting, mal-absorption of vitamin B12 and possible B12 deficiency. Metformin is available in immediate release formulations of 500 mg., 850 mg., and 1000 mg. tablets and in slow and extended release formulations of 500 mg. and 750 mg.

Metformin is often prescribed with rosiglitazone, one form of which is marketed under the trade name Avandia®. While Avandia® has been approved by the Food & Drug Administration (FDA) to treat diabetes mellitus, the FDA recently issued a safety alert on Avandia®, stating that > Safety data from controlled clinical trials have shown that there is a potentially significant increase in the risk of heart attack and heart-related deaths in patients taking Avandia. However, other published and unpublished data from long-term clinical trials of Avandia, including an interim analysis of data from the RECORD trial (a large, ongoing, randomized open label trial) and unpublished reanalyses of data from DREAM (a previously conducted placebo-controlled, randomized trial) provide contradictory evidence about the risks in patients treated with Avandia.
> Patients who are taking Avandia, especially those who are known to have underlying heart disease or who are at high risk of heart attack should talk to their doctor about this new information as they evaluate the available treatment options for their type 2 diabetes.
> FDA's analyses of all available data are ongoing. FDA has not confirmed the clinical significance of the reported increased risk in the context of other studies . . . .

For some patients, the uncertainty of such risks, as well as problems associated with long-term use of Metformin (e.g., need for increased dosages over time), results in an ongoing search for alternatives to address symptoms and underlying physiological conditions related to diabetes mellitus.

Metformin is also prescribed with Amaryl®, available from Sanofi-Aventis and also generically available as glimepiride. Amaryl® is a long-acting, III generation sulfonylurea: 3-ethyl-N,N-bis(3-ethyl-4-methyl-2-oxo-5H-pyrrol-2-yl)-4-methyl-2-oxo-5H-pyrrole-1-carboxamide. Glimepiride lowers blood glucose levels by stimulating pancreatic beta cells to produce more insulin and by inducing increased activity of peripheral insulin intracellular receptors. However, gastrointestinal disturbance can result.

Lantus®, an insulin analogue used to help control blood sugar levels, is prescribed to complement the shorter-acting sulfonylurea drugs. Lantus® is characterized as having a 24-hour duration of action, thereby resembling basal insulin secretion of pancreatic beta cells and minimizing nocturnal hypoglycemia. However, Lantus® typically requires the support of a fast acting insulin taken with food to reduce the effect of meal-derived increase in blood glucose levels.

Exenatide, marketed under the trade name Byetta® and available from Eli Lilly and Company, constitutes a new class of medications approved for treating diabetes. Exenatide is a peptide containing 39 amino acids which functions as an insulin secretagogue and has glucose regulating capabilities. Exenatides are often combined with Metformin and sulfonylureas to improve glucose control. However, exenatides do have some adverse qualities, e.g., they require administration by injection and cause gastrointestinal disturbances in some patients. Exenatide may also increase risk of sulfonylurea-induced hypoglycemia.

Thus, while the above drug therapies, alone and in combination with each other and with other drugs provide significant and life-extending relief from diabetes mellitus, typically, over time, dosages must be increased and new combinations of drugs tried for an individual with diabetes mellitus to maintain acceptable blood glucose levels and a satisfactory life style. As increased dosages and/or combinations are prescribed, treatment costs may increase, the presence of side effects may become manifest, and administration by injections (as compared to oral regimens) may be required. For these reasons, use of nutritional supplements to prevent or control diabetes mellitus has been explored.

U.S. Pat. No. 6,203,819 entitled Dietary Supplement and Method of Treatment for Diabetic Control, discloses a daily nutritional supplement to assist in the metabolism of glucose. So-called "anchor components" include chromium polynicotinate, picolinate, vanadyl sulfate, vitamin E natural, standardized willow bark (as a source of aspirin), magnesium chloride, citrate, fumarate, malate, glutorate, and succinate complex, folic acid and alpha-lipoic acid. This nutritional supplement is more succinctly described in the Summary of the Invention as comprising effectives amounts of sources of chromium, vanadium, magnesium, vitamin E, aspirin, folic acid and alpha-lipoic acid. Essential components claimed include chromium, vanadium and aspirin. However, vanadyl sulfate has been reported to cause gastrointestinal distress and there remains some question about disposition of vanadium in the body after long-term ingestion.

U.S. Pat. No. 6,585,998 entitled Nutraceutical Composition, relates to a nutraceutical composition which is used to maintain normal blood sugar levels and normal levels of non-enzymatic protein glycosylation. The composition requires at least 7 constituents: a tripeptide component, guanidine hydrochloride, alpha-lipoic acid, a brazilin component, an amino acid component, a flavonoid component and a catalase. The addition of selenium is also suggested.

Accordingly, there remains a need for a simplified medical food or nutritional supplement effective to manage blood glucose levels in individuals generally and pre-diabetic individuals in particular, and to assist individuals with diabetes mellitus in the management of their condition.

SUMMARY OF THE INVENTION

The present invention, which relates to medical foods and nutritional supplements found useful for controlling blood glucose levels, includes alpha lipoic acid (herein "α-lipoic acid"), linolenic acid complex, biotin and coenzyme Q-10. Acceptable ranges of the four constituents per day of the preferred formulation of the present invention are as follows:
- α-lipoic acid—200 to 2500 mg.;
- linolenic acid complex—25 to 4000 mg.;
- biotin—5 to 25 mg.; and
- coenzyme Q-10—50 to 500 mg.

A preferred method of manufacturing the medical foods and nutritional supplements of the present invention is to microencapsulate each component, then assemble the microencapsulated components for collective oral administration, for example, in capsules.

DETAILED DESCRIPTION OF PREFERRED EMBODIMENTS

A most preferred formulation of the present invention useful for managing blood glucose levels generally and helping individuals with diabetes mellitus with the management of their diabetes, includes alpha lipoic acid (herein "α-lipoic acid"), linolenic acid complex, biotin and coenzyme Q-10. Acceptable ranges of the four constituents per day of the preferred formulation of the present invention are as follows:
- α-lipoic acid—200 to 2500 milligrams ("mg.");
- linolenic acid complex—25 to 4000 mg.;
- biotin—5 to 25 mg.; and
- coenzyme Q-10—50 to 500 mg.

The α-lipoic acid component of the preferred formations of the present invention, is an antioxidant co-enzyme. One form of α-lipoic acid acceptable for use in the formulations of the present invention is a 600 mg. softgel available from Nature's Life® of Larkspur, Calif.

The "linolenic acid complex" component of the preferred formulations as defined herein contains one or more of the following constituents: palmitic acid, stearic acid, oleic acid, linoleic acid, gamma linolenic acid, alpha linoleic acid, icosenoic acid and erucic acid.

Biotin ($C_{10}H_{16}N_2O_3S$) is sometimes referred to as vitamin B7 or vitamin H. A preferred form of biotin for use in the formulations of the present invention is in 5 mg. capsules.

Coenzyme Q-10 is present in human cells and has a pivotal role in the production of the body's energy, as all ATP is converted to energy with the aid of coenzyme Q-10. A preferred form for use in the formulations of the present invention are softgels containing 100 mg. ubiquinone.

Example 1

The following daily regimen incorporating the four components of the present invention was developed:
- α-lipoic acid—600 mg. tid orally;
- linolenic acid complex—1300 mg. bid orally (for a total per day of 25 mg. linolenic acid, 1910 mg. linoleic acid and 130 mg. gamma linolenic acid);
- biotin—5 mg. tid orally; and
- coenzyme Q-10—100 mg. bid orally.

The above formulation taken orally with or directly after meals is referred to herein as the Example 1 regimen.

The Example 1 regimen was followed by two adult males previously diagnosed with type 2 diabetes mellitus and being treated with prescription drugs, as described below in Examples 2 and 3.

Example 2

A 59 year old Caucasian male 30 pounds over-weight was first diagnosed with type 2 diabetes mellitus in 1996. Treatment initially began with Metformin and Amaryl®, with dosages increasing over time. The Metformin and Amaryl® dosages were then supplemented with Lantus® injections at bedtime in increasing dosage over the next 3 years, as summarized below in Table A. By November 2006, Lantus® dosage was maximized at 55 units qd, and the patient's endocrinologist was recommending adding a fast-acting insulin at mealtime.

TABLE A

| DATES - all dates approximate | METFORMIN dosage | METFORMIN per/day | Other |
|---|---|---|---|
| 1996 to 1997 | 850 mg. bid | 1700 mg. | Amaryl ® 4 mg. qd |
| 1997 to 1998 | 850 mg. bid | 1700 mg. | Amaryl ® mg. qd Starlix ® 120 mg. tid (discontinued after 90 days) |
| 1998 to 1999 | 850 mg. bid | 1700 mg. | Amaryl ® 8 mg. qd |
| 1999 to 2002 | 850 mg. tid | 2550 mg. | Amaryl ® 8 mg. qd |
| 2002 to 2004 | 850 mg. tid | 2550 mg. | Amaryl ® 8 mg. qd Lantus ® 16 units at bedtime increased over three years to 55 units at bedtime |
| 2004 thru first 3 weeks of NOVEMBER 2006 | 850 mg. tid | 2550 mg. | Amaryl ® 8 mg. qd Lantus ® 55 units at bedtime |
| NOVEMBER 2006 for 2 days | 850 mg. tid | 2550 mg. | Amaryl ® 8 mg. qd Lantus ® 48 units at bedtime Example 1 regimen |
| NOVEMBER 2006 to DECEMBER 2006 for 8-10 days | 850 mg. tid | 2550 mg. | Amaryl ® 8 mg. qd Lantus ® decreased from 48 units to 35 units at bedtime Example 1 regimen |

TABLE A-continued

| DATES - all dates approximate | METFORMIN dosage | METFORMIN per/day | Other |
|---|---|---|---|
| DECEMBER 2006 for next 8-10 days | 850 mg. tid | 2550 mg. | Amaryl ® 8 mg. qd<br>Lantus ® decreased from 35 units to 25 units at bedtime<br>Example 1 regimen |
| DECEMBER 2006 for next 7 days | 850 mg. tid | 2550 mg. | Amaryl ® 8 mg. qd<br>Lantus ® 25 units at bedtime<br>Example 1 regimen |
| JANUARY 2007 thru MAY 2007 | 850 mg. tid | 2550 mg. | Amaryl ® 4 mg. qd<br>Lantus ® 25 units at bedtime<br>Example 1 regimen |
| JUNE 2007 thru JULY 2007 | 1000 mg. bid | 2000 mg. | Amaryl ® 4 mg. qd<br>Lantus ® 25 units at bedtime<br>Example 1 regimen |

During the last week of November 2006, the individual supplemented his prescription drug regimen with the Example 1 regimen taken with or directly after meals with all amounts as described in Example 1, except that a liquid coenzyme Q-10 was not precisely measured and was estimated to range from 100 to 150 mg. per day until April 2007, when 100 mg. softgels were substituted. After two days of the Example 1 regimen, the individual's blood glucose level was substantially lower, and he decreased his Lantus® injections from 55 to 45 units. During the next 8-10 days, while maintaining the Example 1 regimen, his blood glucose levels continued to decrease such that he was able to decrease his Lantus® injections in a step-wise fashion over this time period from 45 to 35 units. During the next 7 days, while continuing to maintain the Example 1 regimen, the individual decreased his Lantus® injections from 35 to 25 units at bedtime. In January 2007, the individual was able to decrease his Amaryl® dosage from 8 mg. per day to 4 mg. per day. In June 2007, the dosage of Metformin was decreased from 2550 mg. per day to 2000 mg. per day, while still maintaining acceptable blood glucose levels.

Example 3

A 58 year old Caucasian male 70 pounds overweight was first diagnosed with type 2 diabetes mellitus in 1999, after which treatment with Metformin, Avandia® and Byetta® progressed as is summarized in Table B below.

TABLE B

| DATES - all dates approximate | METFORMIN dosage | METFORMIN per/day | Other |
|---|---|---|---|
| 1999 to 2001 | 500 mg. bid | 1000 mg. | |
| 2001 to 2003 | 500 mg. bid | 1000 mg. | Avandia ® 4 mg. qd |
| 2003 to 2005 | 500 mg. tid | 1500 mg. | Avandia ® 4 mg. qd |
| 2005 thru NOVEMBER 2006 | 1000 mg. bid | 2000 mg. | Avandia ® 4 mg. qd<br>Byetta ® 10 µg. bid |
| DECEMBER 2006 | 1000 mg. bid | 2000 mg. | Avandia ® 4 mg. qd<br>Byetta ® 10 µg. bid<br>Example 1 regimen |
| JANUARY 2007 thru MARCH 2007 | 500 mg. bid | 1000 mg. | Byetta ® 10 µg. bid<br>Avandia ® 4 mg. qd<br>Example 1 regimen |
| APRIL 2007 thru JULY 2007 | 500 mg. qd | 500 mg. | Byetta ® 10 µg. bid<br>Example 1 regimen |

As can be seen above, the individual's prescription drug regimen was increasing in dosage of Metformin over the years, and upon supplementing the prescription drug program with the Example 1 regimen, over time the individual was able to omit the Avandia® and reduce the Metformin dosage to a minimal level.

Without knowing the precise mechanism(s) by which the formulations of the present invention contribute to the maintenance of acceptable blood glucose levels in individuals with type 2 diabetes mellitus while decreasing dosages of Metformin and other prescription drugs which otherwise over time were requiring increased dosages, it is believed that the components of the present invention work synergistically to normalize insulin receptors damaged by the presence of excess insulin in the body. The excess insulin, which is believed over time to cause a trend of steadily increasing down-regulation of the insulin receptors, is at least partially reversed when the formulations of the present invention are orally administered.

While the components of the Example 1 formulation were administered above periodically during the day, orally, in individual softgels and capsules for each component, and so the components may be purchased individually, a most preferred form for administration of the formulations of the present invention is a mixture wherein one or more, and preferably all four, and most preferably three of the components are separately microencapsulated and then packaged together for oral administration in capsules or other forms. In the most preferable form, the alpha-lipoic, coenzyme Q-10 and biotin are micro encapsulated and the linolenic acid complex becomes the matrix in which the microencapsulated components are embedded. Microencapsulation processes are well known to those of skill in the art, but have not been used to package medical foods/nutritional supplements for use as described herein.

When administering mixtures of the separately microencapsulated components of the medical foods and/or nutritional supplements of the present invention, preferred recommended dosages are 5% to 95% of each of the constituents described above. Most preferred dosages are from 50% to 75% of each of the constituents described above. These substantially decreased dosages result from controlled and sustained delivery of the active substances achieved by the use of microcapsules, so that substantially more of each component of the formulations of the present invention reaches the blood circulation. Most preferred ranges of the four constituents per day of the formulation of the present invention when one or more are of the constituents are microencapsulated are as follows:

α-lipoic acid—50 to 1875 milligrams ("mg.");
linolenic acid complex—12.5 to 3000 mg.;
biotin—2.5 to 18.75 mg.; and
coenzyme Q-10—25 to 375 mg.

Another preferred delivery form of the formulations of the present invention is packaged as a mixture, preferably microencapsulated, in small impermeable, disposable packages such as packets (e.g., 1½"×2" in size) or small tubes (e.g., ¼" diameter×2" in length) which may be foil, plastic, or other disposable material. In these configurations, the contents of the packages containing the formulations are mixed with food or a cold liquid.

Alternate formulations and regimens of the present invention include α-lipoic acid, linolenic acid complex, biotin and coenzyme Q-10 and also thiamine, often referred to as vitamin B1. Recommended thiamine dosages to be combined with the formulations of the present invention are from 5 to 25 mg. per day. It is further contemplated that vitamin B12 could be substituted for the thiamine, in dosages of from 20 to 60 μg. per day. In yet another embodiment, a B vitamin complex is combined with the formulations of the present invention. Other formulations and regimens of the present invention include α-lipoic acid, linolenic acid complex, biotin and coenzyme Q-10 and also L-carnatine.

While it is contemplated that further components as described above may be combined in the formulations of the present invention, or administered in conjunction with the formulations of the present invention, a further embodiment of the present invention consists essentially of α-lipoic acid, linolenic acid complex, biotin and coenzyme Q-10. While acceptable ranges of daily dosages are listed below α-lipoic acid—200 to 2500 mg.;
linolenic acid complex—25 to 4000 mg.;
biotin—5 to 25 mg.; and
coenzyme Q-10—50 to 500 mg, any of the other formulations described herein may be limited to consist essentially of the stated ingredients at the stated ingredient dosages or dosage ranges.

While there have been described above the principles of the present invention in conjunction with preferred embodiments thereof, it is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features which are already known and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The applicants hereby reserve the right to formulate new claims to such features and/or combinations of such features during the prosecution of the present application or of any further application derived therefrom.

The invention claimed is:

1. A medical food and/or nutritional supplement for oral administration in mammals for managing blood glucose levels by decreasing a need for diabetic medication, comprising:
α-lipoic acid;
linolenic acid complex comprising linolenic acid, linoleic acid and γ-linolenic acid;
biotin; and
coenzyme Q-10.

2. The medical food and/or nutritional supplement of claim 1 wherein a daily dosage comprises:
α-lipoic acid-200 to 2500 mg.;
linolenic acid complex-25 to 4000 mg.;
biotin-5 to 25 mg.; and
coenzyme Q-10-50 to 500 mg.

3. The medical food and/or nutritional supplement of claim 1 wherein a daily dosage comprises:
α-lipoic acid—at least 1800 mg.;
linolenic acid complex—at least 2600 mg.;
biotin—15 mg.; and
coenzyme Q-10—200 mg.

4. The medical food and/or nutritional supplement of claim 1, wherein a daily dosage comprises
α-lipoic acid—about 1350 mg.;
linolenic acid complex—about 1432.5 mg.;
biotin—about 11.25 mg; and
coenzyme Q-10—about 150 mg.

5. The medical food and/or nutritional supplement of any of claims 1-3, further comprising vitamin B1.

6. The medical food and/or nutritional supplement of any of claims 1-3, further comprising a vitamin B complex.

7. The medical food and/or nutritional supplement of any of claims 1-3, further comprising L-carnatine.

8. A nutritional supplement for oral administration in mammals for managing blood glucose levels by decreasing a need for diabetic medication, consisting essentially of:
α-lipoic acid;
linolenic acid complex comprising linolenic acid, linoleic acid and γ-linolenic acid;
biotin; and
coenzyme Q-10.

* * * * *